US008841712B2

(12) United States Patent
Rajagopal et al.

(10) Patent No.: US 8,841,712 B2
(45) Date of Patent: Sep. 23, 2014

(54) NANO-PILLAR TRANSISTOR FABRICATION AND USE

(71) Applicant: California Institute of Technology, Pasadena, CA (US)

(72) Inventors: Aditya Rajagopal, Irvine, CA (US); Axel Scherer, Barnard, VT (US); Michael D. Henry, Altadena, CA (US); Sameer Walavalkar, Studio City, CA (US); Thomas A. Tombrello, Altadena, CA (US); Andrew P. Homyk, South Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 13/852,480

(22) Filed: Mar. 28, 2013

(65) Prior Publication Data

US 2014/0070286 A1    Mar. 13, 2014

Related U.S. Application Data

(60) Provisional application No. 61/617,528, filed on Mar. 29, 2012.

(51) Int. Cl.
*H01L 29/76* (2006.01)
*G01N 27/327* (2006.01)
*H01L 29/66* (2006.01)
*H01L 29/78* (2006.01)

(52) U.S. Cl.
CPC ............ *H01L 29/78* (2013.01); *G01N 27/3275* (2013.01); *H01L 29/66477* (2013.01)
USPC .................................. 257/288; 257/E51.005

(58) Field of Classification Search
CPC ..................................................... G01N 27/414
USPC ............................................................ 257/288
See application file for complete search history.

(56) References Cited

U.S. PATENT DOCUMENTS 6,130,098 A    10/2000    Handique et al.
6,605,519 B2    8/2003    Lishan
(Continued)

FOREIGN PATENT DOCUMENTS

KR    10-2010-0048380    11/2010
KR    10-2012-0021683    3/2012

OTHER PUBLICATIONS

Restriction Requirement mailed on Jun. 13, 2014 for U.S. Appl. No. 13/852,476, filed Mar. 28, 2013 in the name of Aditya Rajagopal.
International Search Report issued for PCT Application No. PCT/US2013/034315 filed on Mar. 28, 2013 in the name of California Institute of Technology. mail date: Jan. 28, 2014.
(Continued)

*Primary Examiner* — Thao X Le
*Assistant Examiner* — Patricia Reddington
(74) *Attorney, Agent, or Firm* — Steinfl & Bruno, LLP

(57) ABSTRACT

A field effect nano-pillar transistor has a pillar shaped gate element incorporating a biomimitec portion that provides various advantages over prior art devices. The small size of the nano-pillar transistor allows for advantageous insertion into cellular membranes, and the biomimitec character of the gate element operates as an advantageous interface for sensing small amplitude voltages such as transmembrane cell potentials. The nano-pillar transistor can be used in various embodiments to stimulate cells, to measure cell response, or to perform a combination of both actions.

12 Claims, 6 Drawing Sheets

(56) References Cited

U.S. PATENT DOCUMENTS

| | | |
|---|---|---|
| 7,368,370 B2 | 5/2008 | Jain et al. |
| 8,017,938 B2 | 9/2011 | Gomez et al. |
| 2002/0164884 A1 | 11/2002 | Lishan |
| 2008/0035494 A1 | 2/2008 | Gomez et al. |
| 2008/0070354 A1 | 3/2008 | Jain et al. |
| 2009/0177144 A1 | 7/2009 | Masmanidis et al. |
| 2010/0268078 A1 | 10/2010 | Scarantino et al. |
| 2011/0044694 A1 | 2/2011 | Scherer et al. |
| 2011/0218490 A1 | 9/2011 | Ocvirk et al. |
| 2011/0288391 A1 | 11/2011 | Rao et al. |
| 2014/0030819 A1* | 1/2014 | Rajagopal et al. ............ 436/501 |

OTHER PUBLICATIONS

Written Opinion issued for PCT Application No. PCT/US2013/034315 filed on Mar. 28, 2013 in the name of California Institute of Technology. mail date: Jan. 28, 2014.

International Search Report issued for PCT Application No. PCT/US2013/034297 filed on Mar. 28, 2013 in the name of California Institute of Technology. mail date: Jan. 24, 2014.

Written Opinion issued for PCT Application No. PCT/US2013/034297 filed on Mar. 28, 2013 in the name of California Institute of Technology. mail date: Jan. 24, 2014.

* cited by examiner

US 8,841,712 B2

NANO-PILLAR TRANSISTOR FABRICATION AND USE

CROSS REFERENCE TO RELATED APPLICATIONS

This application claims priority under 35 U.S.C. §119(e) from U.S. Provisional Patent Application No. 61/617,528 entitled "Transmembrane Pillar FET" filed on Mar. 29, 2012, which is incorporated herein by reference in its entirety. Furthermore, the present application is related to U.S. Pat. application Ser. No. 13/852,476 filed on even date herewith, entitled "Sensor Probe for Bio-sensing and Chemical-sensing Applications," which is also incorporated herein by reference in its entirety.

STATEMENT OF FEDERAL GOVERNMENT SUPPORT

This invention was made with government support under W911NF-07-1-0277 awarded by the Army Research Office. The government has certain rights in the invention.

FIELD

The present teachings relate to nano-transistors. In particular, the present teachings relate to fabricating and using a field-effect nano-transistor having a biomimitec characteristic.

BACKGROUND

Extracellular electrodes are often too large for use in applications where the target cells have small size. For example, extracellular electrodes are generally too big for measuring single neuron behavior. Even when miniaturized, many prior art electrodes suffer from other handicaps such as being vibration sensitive and causing cell death due to materials incompatibility. It is therefore desirable to provide an implantable electrode device that is not only small in size but also contains materials that are suitable for benign implantation of the device into cellular entities.

SUMMARY

According to a first aspect of the present disclosure, a method of fabricating a nano-pillar transistor, includes the following steps: providing a polymer coating upon a silicon substrate; using electron beam lithography to fabricate a mask pattern in the polymer coating; depositing an alumina film upon the mask pattern; creating a hard-etch mask by using a solvent to remove a portion of the alumina film and a portion of the polymer coating; using the hard-etch mask for executing a first etching procedure to create a plurality of nano-pillars; executing a second etching procedure for reducing a diameter of each of the plurality of nano-pillars, wherein the plurality of nano-pillars having the reduced diameter constitutes a plurality of gates of an array of nano-pillar transistors; using an ion beam procedure to introduce dopants for fabricating each of a source region and a drain region adjacent to each of the plurality of gates; applying electron beam annealing of the dopants; using one of an ion milling procedure or a reactive ion etching procedure to remove deposited alumina film from a top portion of each of the plurality of gates; applying metallization upon each of the plurality of gates and upon each of the source region and the drain region adjacent to each of the plurality of gates; and depositing alternating metal stacks between each of the metallized plurality of gates, wherein the alternating metal stacks mimic a hydrophilic-hydrophobic-hydrophilic structure of a cellular membrane.

According to a second aspect of the present disclosure, a nano-pillar includes a planar substrate and a biomimitec gate. The planar substrate includes a source segment and a drain segment. The biomimetic gate, which is arranged between the source segment and the drain segment, has a pillar structure with a linear axis oriented orthogonal to the planar substrate, the pillar structure incorporating a first platinum-gold-platinum metal portion that mimics a hydrophilic-hydrophobic-hydrophilic structure of a cellular membrane.

According to a third aspect of the present disclosure, a system includes a nano-pillar transistor having a biomimetic gate configured as a pillar structure with a linear axis of the pillar structure oriented orthogonal to a substrate. The pillar structure incorporates a platinum-gold-platinum metal portion that mimics a hydrophilic-hydrophobic-hydrophilic structure of a cellular membrane.

Further aspects of the disclosure are shown in the specification, drawings and claims of the present application.

BRIEF DESCRIPTION OF THE DRAWINGS

Many aspects of the present disclosure can be better understood with reference to the following drawings. The components in the drawings are not necessarily drawn to scale. Instead, emphasis is placed upon clearly illustrating various principles. Moreover, in the drawings, like reference numerals designate corresponding parts throughout the several views.

DETAILED DESCRIPTION

Throughout this description, embodiments and variations are described for the purpose of illustrating uses and implementations of the inventive concept. The illustrative description should be understood as presenting examples of the inventive concept, rather than as limiting the scope of the concept as disclosed herein. It will be understood that various labels such as, for example, nano-pillar transistor, nano-transistor, field effect nano-pillar transistor, field effect transistor, contacts, and terminals are used herein in an alternative manner as a matter of convenience and are to be interpreted appropriately in the context of the description, without attaching illogical and unusual restrictions to these terms. It will be also understood that phrases such as plurality of nano-pillar transistors, plurality of gates, and plurality of nano-pillar field effect transistors are used herein in an alternative manner as a matter of convenience and are to be interpreted appropriately in the context of the description, without attaching illogical and unusual restrictions to these phrases.

Field effect transistors can be used as sensors for a variety of applications, including bio-sensing applications. In accordance with the disclosure, a field effect nano-pillar transistor has a pillar shaped gate element incorporating a biomimitec portion that provides various advantages over prior art devices. The small size of the nano-pillar transistor disclosed herein allows for advantageous insertion into cellular membranes, and the biomimitec character of the gate element operates as an advantageous interface for sensing small amplitude voltages such as trans-membrane cell potentials. The nano-pillar transistor can be used in various embodiments to stimulate cells, to measure cell response, or to perform a combination of both actions.

In some example embodiments, the nano-pillar transistor disclosed herein can be configured to execute a multiplexed mode of operation (for example, a time multiplexed mode of operation) whereby the same nano-pillar transistor can be used to inject a current into a cell (writing to the cell) and then measure the electrical response to the current injection (reading the cell).

Figure 1:
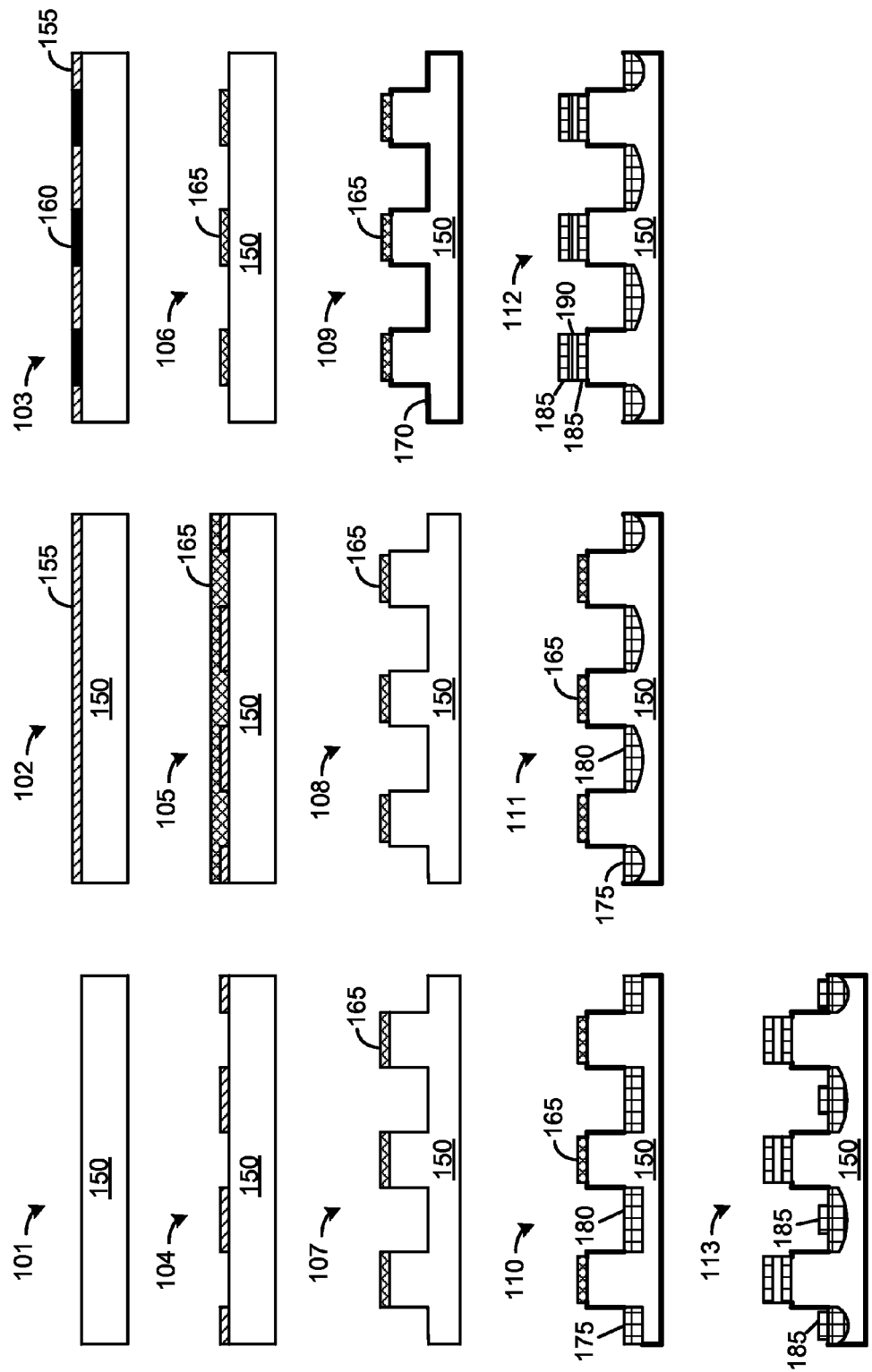
FIG. 1 shows various stages during fabrication of an array of nano-pillar transistors in accordance with the disclosure.

Attention is now drawn to FIG. 1, which shows various stages during fabrication of an array of nano-pillar transistors in accordance with the disclosure. Each of the stages is referenced by a numeric label, and these numerical labels will be used below as a matter of convenience for purposes of description.

In stage 101, a highly doped silicon wafer 150 is spin coated with a polymer (not shown). In one example embodiment, the polymer is poly-methyl-methacrylate (PMMA). In stage 102, a soft mask 155 is written into the polymer using electron beam lithography for example. The resulting mask pattern is shown in stage 103, where the dark shaded areas 160 indicate areas in which material is to be removed in subsequent stages of fabrication. In stage 104, a polymer development procedure is performed, followed (in stage 105) by sputter deposition of an alumina film 165. In one example implementation, the alumina film is about 45 nm thick. In another example implementation, RF sputtering is used to deposit stoichiometric $Al_2O_3$.

In stage 106, excess alumina and polymer is removed, leaving behind a hard etch-mask that is in direct contact with the silicon wafer 150. In one example implementation, excess alumina and polymer is removed by lift-off in dichloromethane.

In stage 107, a plurality of silicon nano-pillars are defined using deep reactive ion etching techniques. Each of the plurality of silicon nano-pillars is used to fabricate an individual biomimetic gate terminal of an individual nano-pillar field-effect transistor. Side-wall passivation is achieved by using cryogenic cooling of the sidewalls of the nano-pillars. In one example implementation, the cryogenic cooling temperature is about −140° Celsius. A 90 sccm:10 sccm SF6:O2 gas ratio may be used during the etching. An inductively coupled plasma power of 1800 W and a forward power of about 5 W may be used to define silicon nano-pillars that are between 100 nm and 10 microns tall. The height may be selected in order to provide aspect ratios (height:width) extending up to 100:1.

In stage 108, a short, under-passivated Bosch etch is used to shrink the width of the plurality of silicon nano-pillars, followed by oxidization (stage 109) to provide isolation between the silicon nano-pillars. The oxidation stage is carried out when the silicon nano-pillars are intended for fabricating MOSFET, JFET, or MESFET types of nano-transistors. However, stage 109 may be omitted when fabricating other types of nano-transistors.

In stage 110, focused-ion beam lithography is used for introducing dopants into silicon substrate 150 in order to define source segment 175 and drain segment 180. In stage 111, electron-beam annealing of the dopants is performed.

In stage 112, source, drain and gate metallization is carried out using electron-beam evaporation techniques. When the plurality of silicon nano-pillars (gates) are intended for bio-sensing applications, a biomimitec structure is fabricated upon each of the nano-pillars. In one embodiment, the biomimitec structure is a platinum-gold-platinum metal stack formed of a gold layer 190 sandwiched between a pair of platinum layers 185. The platinum-gold-platinum metal stack mimics the hydrophilic-hydrophobic-hydrophilic structure of cellular membranes, allowing for easy integration into biological systems. In stage 103, metal contacts are fabricated upon each of the source segment 175 and drain segment 180. In one implementation, the metal used is gold. Sulfur chemistry is then used to form Au—S thiol bonds and complete the fabrication of the array of nano-pillar transistors.

After stage 113 is completed, a singulating procedure is performed to produce individual nano-pillar transistors from the array of nano-pillar transistors.

Figure 2:
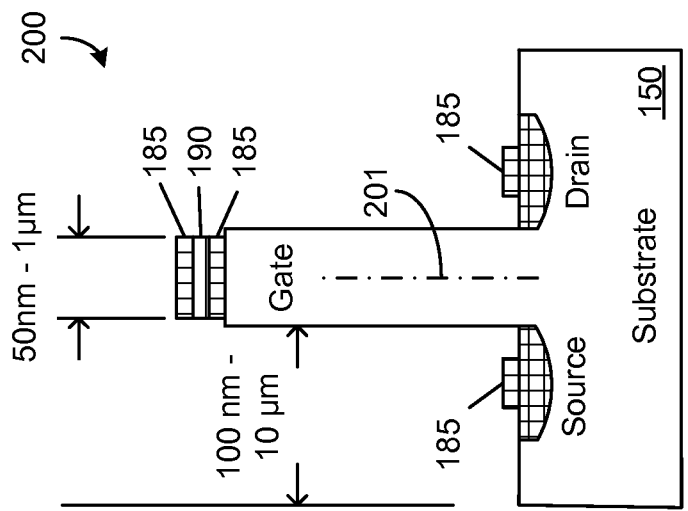
FIG. 2 shows a structural cross-section of a nano-pillar transistor in accordance with the disclosure.

FIG. 2 shows a structural cross-section of one such individual nano-pillar transistor 200 in accordance with the disclosure. The structural cross-section provides an indication of some dimensional values that may be used in the nano-pillar transistor. Furthermore, the gate terminal of the nano-pillar transistor, which is located between the source and the drain, has a pillar structure with a linear axis 201 oriented orthogonal to the planar substrate 150.

Figure 3:
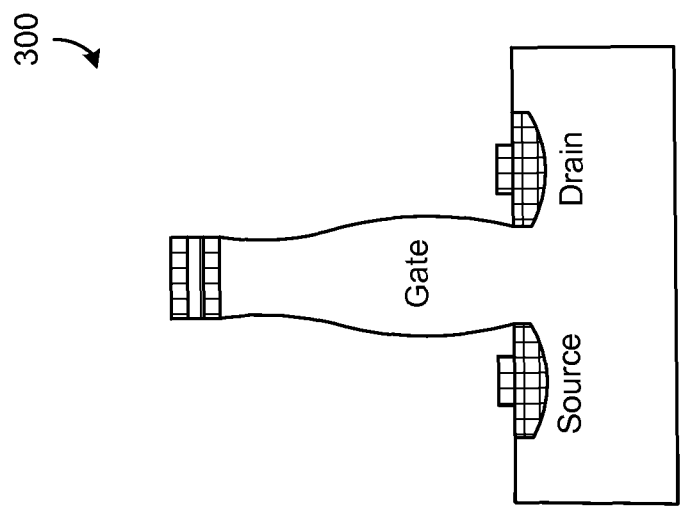
FIG. 3 shows an example nano-pillar transistor having a gate that is shaped to provide improved anchoring in cellular entities in accordance with the disclosure.

FIG. 3 shows a nano-pillar transistor 300 having a gate that is shaped to provide improved anchoring in cellular membranes. While one example shape is indicated in the embodiment shown in FIG. 3, it will be understood that in other embodiments, the gate can be fabricated in a variety of shapes including, for example, one having a serrated surface texture, a tapered straight line profile, a tapered curved profile, a multi-curved profile etc. These various shapes and surface textures can be fabricated for example by using repeated under-passivated and critically-passivated pseudo-Bosch etches. The serrated surface can be based on the type of anchoring desired, such as for anchoring on to neurons or to other types of biological surfaces.

A nano-pillar transistor in accordance with the disclosure can be used in a variety of devices, circuits and systems. A few examples are described below.

Figure 4:
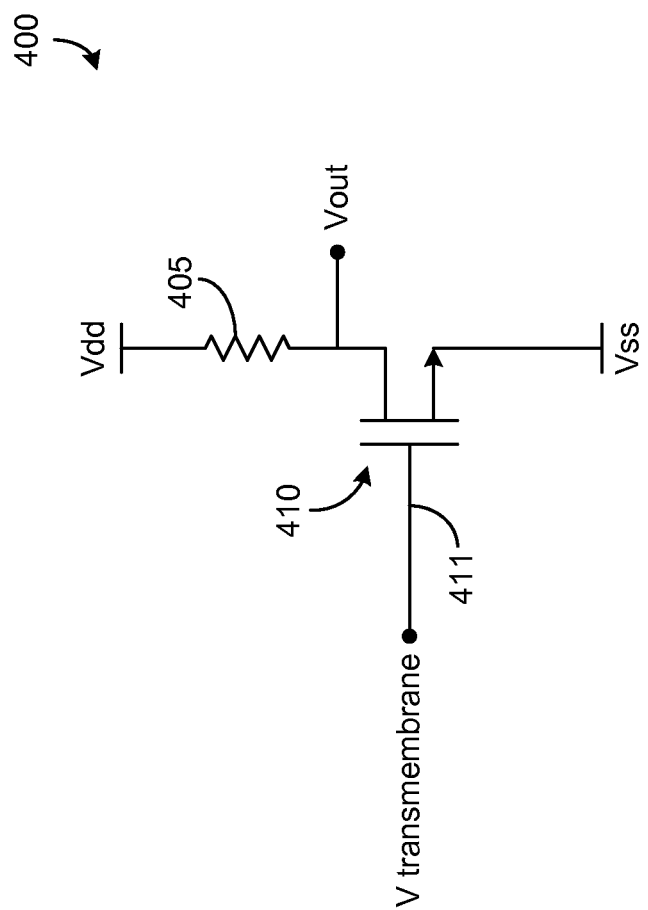
FIG. 4 shows a common-source voltage amplifier incorporating a nano-pillar transistor in accordance with the disclosure.

FIG. 4 shows a common-source voltage amplifier 400 incorporating a nano-pillar transistor 410 in accordance with the disclosure. A transmembrane cellular potential, which in one implementation is in the range of −200 mV to 200 mV with respect to solution potential, affects a change to the gate 411 of nano-pillar transistor 410. This change results in placing nano-pillar transistor 410 in a saturated conduction state. Careful tuning of gate dimensions such as length, width, and geometry can be used to adjust gain, sensitivity, and bandwidth parameters.

Figure 5:
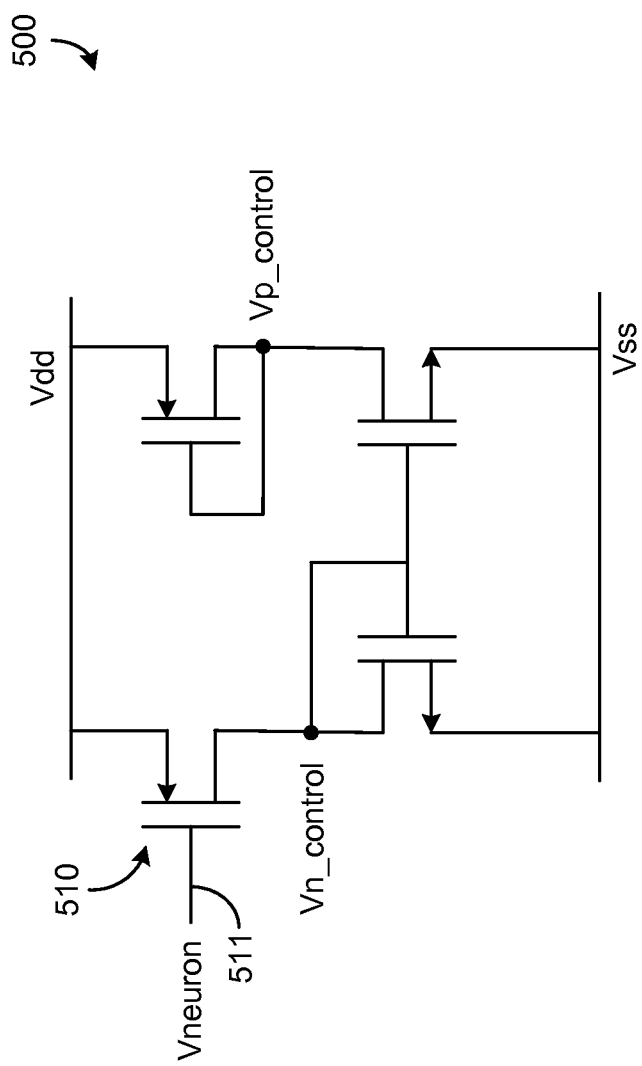
FIG. 5 shows a current mirror circuit incorporating a nano-pillar transistor in accordance with the disclosure.
Figure 6:
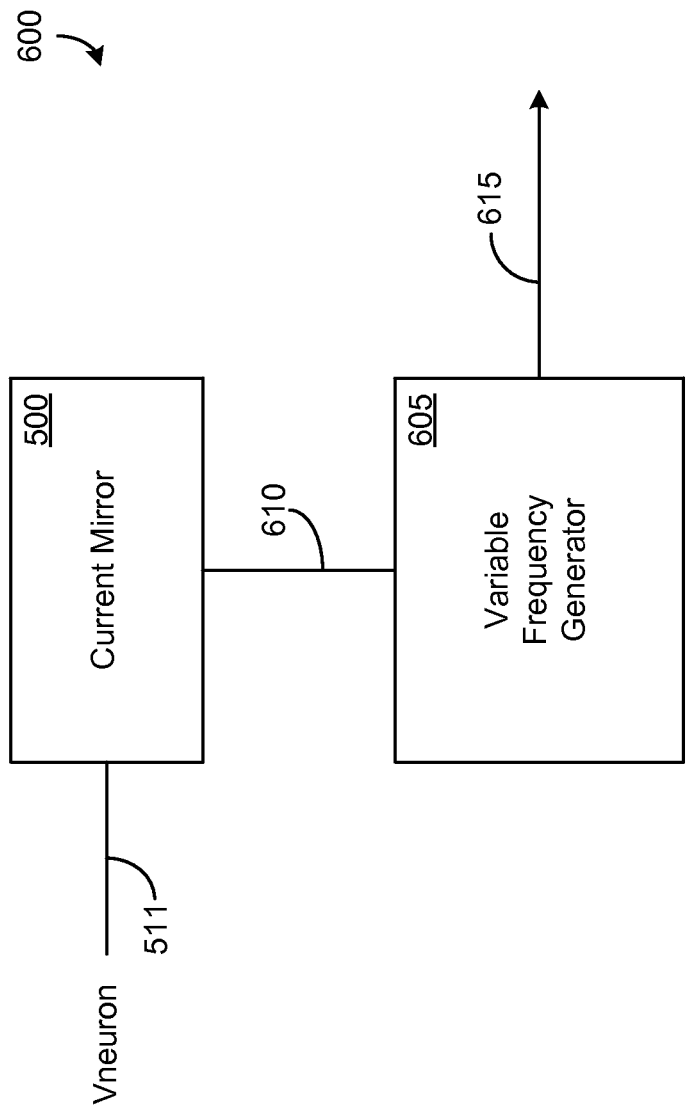
FIG. 6 shows a detection system incorporating the current mirror circuit shown in FIG. 5.

FIG. 5 shows a current minor circuit 500 incorporating a nano-pillar transistor 510 in accordance with the disclosure. It should be understood that in some embodiments the other transistors shown in FIG. 5 may also be nano-pillar transistors, while in other embodiments other types of transistors may be used. A neuron voltage at gate 511 of nano-pillar transistor 510 is converted by current mirror circuit 500 into a current that can be decoded by various detection circuits, such as, for example, detection circuit 600 shown in FIG. 6.

Detection circuit 600 includes current minor 500 coupled to a variable frequency generator 605. In some implementations, variable frequency generator 605 includes a voltage controlled oscillator (not shown).

In one example embodiment, current mirror 500 generates a first control current in response to a first neuron voltage present on line 511. The first control current is propagated via line 610 from current mirror 500 to variable frequency generator 605. Furthermore, current minor 500 generates a second control current in response to a second neuron voltage present on line 511. The second control current is also propagated via line 610 from current minor 500 to variable frequency generator 605.

Variable frequency generator 605 generates a first signal at a first frequency when the first control current is provided via line 610. The first signal is output on line 615. Variable frequency generator 605 generates a second signal at a second frequency when the second control current is provided via line 610. The second signal is also output on line 615. The occurrence of the first and second signals are indicative of different voltage levels produced by one or more neurons and can be used for carrying out various measurement procedures.

Drawing attention once again to FIG. 1, it will be understood that as a result of the fabrication process, which can be carried out using standard CMOS fabrication techniques, nano-pillar transistor 510 can be incorporated into various types of integrated circuits. For example, a nano-pillar transistor in accordance with the disclosure can be fabricated in the form of an application specific integrated circuit (ASIC) for use as an integrated sensor device.

Furthermore, a plurality of nano-pillar transistors can be coupled together in a parallel configuration in order to provide more current capacity and/or to reduce parasitic capacitances and resistances in various measurement applications.

All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments/implementations of the disclosure have been described. Nevertheless, it will be understood that various modifications may be made without departing from the spirit and scope of the present disclosure. Accordingly, other embodiments are within the scope of the following claims.

What is claimed is:

1. A method of fabricating a nano-pillar transistor, comprising:
   providing a polymer coating upon a silicon substrate;
   using electron beam lithography to fabricate a mask pattern in the polymer coating;
   depositing an alumina film upon the mask pattern;
   creating a hard-etch mask by using a solvent to remove a portion of the alumina film and a portion of the polymer coating;
   using the hard-etch mask for executing a first etching procedure to create a plurality of nano-pillars;
   executing a second etching procedure for reducing a diameter of each of the plurality of nano-pillars, wherein the plurality of nano-pillars having the reduced diameter constitutes a plurality of gates of an array of nano-pillar transistors;
   using an ion beam procedure to introduce dopants for fabricating each of a source region and a drain region adjacent to each of the plurality of gates;
   applying electron beam annealing of the dopants;
   using one of an ion milling procedure or a reactive ion etching procedure to remove deposited alumina film from a top portion of each of the plurality of gates;
   applying metallization upon each of the plurality of gates and upon each of the source region and the drain region adjacent to each of the plurality of gates; and
   depositing alternating metal stacks between each of the metallized plurality of gates, wherein the alternating metal stacks mimic a hydrophilic-hydrophobic-hydrophilic structure of a cellular membrane.

2. The method of claim 1, further comprising:
   after executing the second etching procedure, using an oxidizing procedure to increase isolation between each of the plurality of gates; and
   after the depositing of alternating metal stacks, exposing the array of nano-pillar transistors to sulfur chemistry.

3. The method of claim 2, further comprising:
   singulating the array of nano-pillar transistors to produce a plurality of transistor packages, each package containing at least one nano-pillar transistor.

4. The method of claim 1, wherein the polymer coating is a poly-methyl-methacrylate coating and wherein the ion beam procedure comprises one of a diffusion procedure, a lithographic procedure or an implantation procedure.

5. The method of claim 4, wherein the alumina film has a thickness of about 45 nm.

6. The method of claim 4, further comprising:
   using cryogenic cooling for side wall passivation during the first etching procedure.

7. The method of claim 4, wherein executing the first etching procedure comprises using a sulfur hexafluoride to oxygen (SF6:O2) gas ratio of about 90 sccm:10 sccm.

8. The method of claim 7, wherein each of the plurality of nano-pillars created by executing the first etching procedure ranges in height from about 100 nm to about 10 µm.

9. The method of claim 7, wherein each of the plurality of nano-pillars created by executing the first etching procedure has an aspect ratio of height to weight extending up to an upper limit of about 100:1.

10. The method of claim 4, wherein executing the second etching procedure for reducing the diameter of each of the plurality of nano-pillars comprises an under-passivated Bosch etching procedure.

11. The method of claim 4, wherein applying metallization comprises using an electron-beam evaporation procedure.

12. A nano-pillar transistor fabricated in accordance with the method of claim 1.

* * * * *